United States Patent [19]
Jordan

[11] 4,446,856
[45] May 8, 1984

[54] ORTHOTIC DEVICE
[75] Inventor: R. Paul Jordan, Northport, N.Y.
[73] Assignee: The Langer Biomechanics Group, Inc., Deer Park, N.Y.
[21] Appl. No.: 331,913
[22] Filed: Dec. 18, 1981
[51] Int. Cl.³ .............................................. A61F 5/00
[52] U.S. Cl. .............................. 128/80 R; 128/80 H; 128/83.5
[58] Field of Search ................ 128/80 R, 80 H, 87 R, 128/81 R, 83, 83.5, 615, 89 R

[56] References Cited
U.S. PATENT DOCUMENTS

| | | | |
|---|---|---|---|
| 2,725,648 | 12/1955 | Kirk et al. | 128/83.5 X |
| 3,731,323 | 5/1973 | Glancy | 128/83.5 |
| 3,955,565 | 5/1976 | Johnson, Jr. | 128/89 R |
| 4,057,056 | 11/1977 | Payton | 128/83.5 |

FOREIGN PATENT DOCUMENTS 303241  11/1932  Italy .................................. 128/615

*Primary Examiner*—John D. Yasko
*Attorney, Agent, or Firm*—James & Franklin

[57] ABSTRACT

An orthotic device that includes a boot for immobilizing the ankle and foot against relative movement and holds them in a neutral position of maximal joint congruency while providing a sole having a platform for causing the foot to describe a heel to toe rocking movement such that the leg of the user is flexed at the knee and a pivotting motion is induced at the hip joint during walking.

28 Claims, 7 Drawing Figures

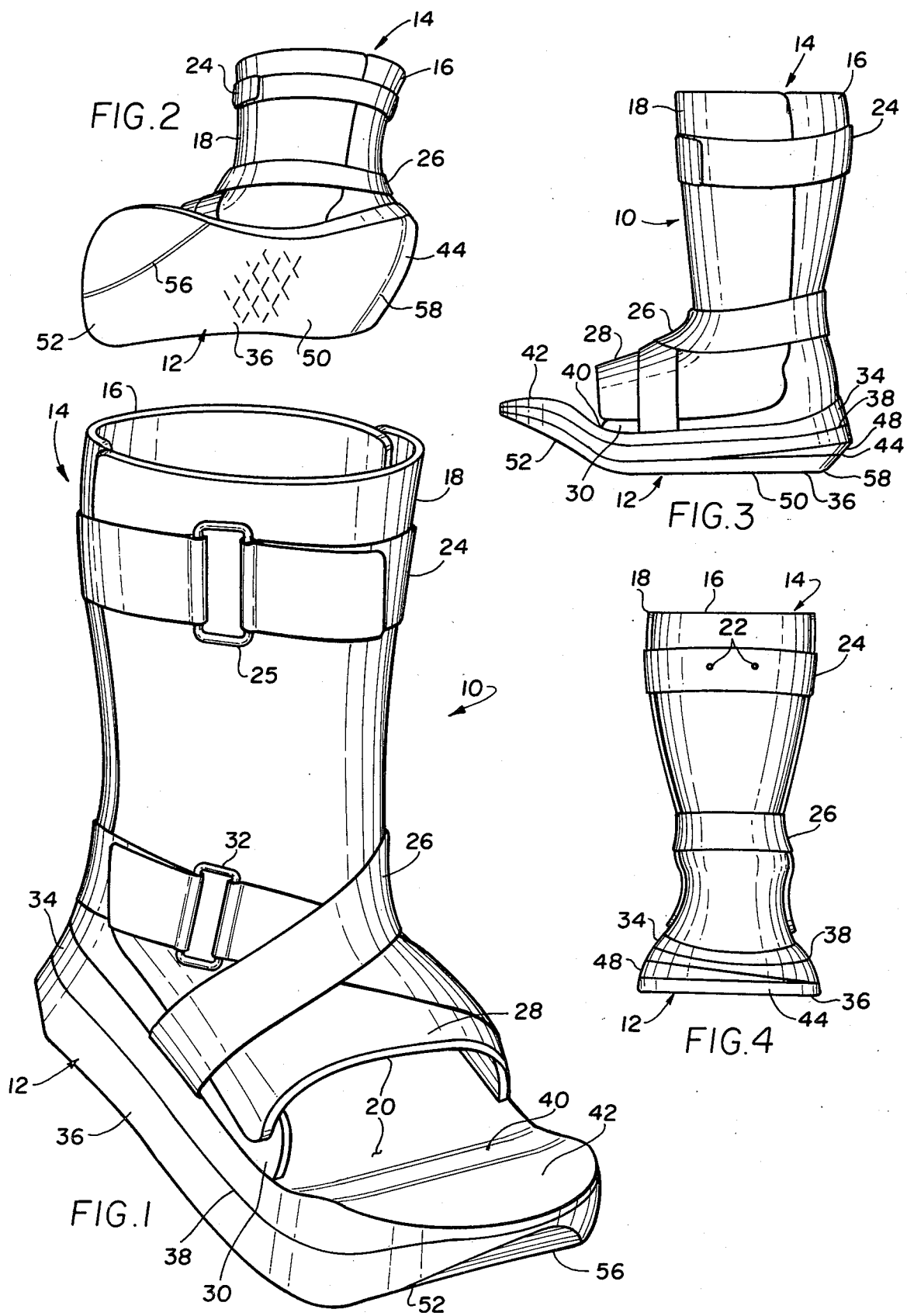

ORTHOTIC DEVICE

The present invention relates to rehabilitative orthotics or devices that function as mobilizing force applicators by the use of mechanics to restore functions to the body of individuals with physical limitations that have been acquired or that are congenital. More particularly, the present invention teaches a tone reducing ankle-foot orthosis for the dynamic rehabilitation of ambulating problems experienced by brain damaged persons as those afflicted with cerebral palsy, stroke, clubfoot, spina bifida, and the like.

Persons who, more often from birth, although sometimes later in life, suffer from motor dysfunction generally find it incapable to walk normally. Their gait is stilted. That is to say, in many instances for them to walk at all, it is characteristic for them to raise their arms and elbows in an almost shoulder high elevated position. The hands are extended forward in front of and across the chest; the legs and hip are stiff jointed so that the legs and hip are relatively immobile with respect to each other.

For a person of this type to ambulate, they swing at their shoulders to move the hips and rigid legs in a sliding motion over the walking surface moving the hip in a forward and rearward direction. The whole side of the body is substantially rigid and stiff and rotates about a vertical axis extending substantially through the length of the body. Such persons are incapable of or have not learned how to bend or flex the hip joint nor are they capable of flexing at the knee joint. Hence, ambulating movements are stilted, difficult and a painful experience to be avoided or held to the minimum. At times some of the children, more so than the adults, are faced with toe-in or toe-out conditions.

In the past orthopedists and podiatrists have attempted to help such persons by fitting them with a boot made from a plaster cast of the leg and sometimes of the foot. It was thought that if the boot were made while the leg, foot and ankle were in the position of a normal person, this would enable the afflicted person to walk flat on the walking surface. This misunderstanding is typified in the disclosures of the U.S. Pat. Nos. 3,713,437, 3,765,409 and 3,976,059 and in the West German Pat. No. 937846.

Persons of the type generally afflicted with the problems here described usually walk on their toes with the foot in a drop foot position. The reason for this is that when and if the metatarsals come into contact with any hard surface, they automatically signal the muscles in the leg and throughout the body to tone or tighten and stiffen. This produces spastic muscles which is, at times, referred to as muscle tone.

These muscle spasms produce such reactions throughout the body that the body tends to overcompensate elsewhere for the difficulties being experienced by the foot when the metatarsals come into contact with a surface. The present invention recognizes this problem and obviates the same by the use of a boot which, although it immobilizes the ankle and foot against relative movement, also supports the same in their neutral position of maximal joint contact or joint to joint congruency. In so doing, instead of bringing the foot and ankle down to the walking surface, the boot builds up to the shape of the foot and ankle while the same are in their neutral position and the muscles are fully relaxed.

The present invention recognizes the problems as aforedescribed and the prior misunderstandings that have fostered them. The present invention provides an orthotic device which, although it immobilizes and fuses the foot and ankle to inhibit their relative movement, induces and imparts mobilizing movements and moments to the foot and leg during ambulation that causes the same to produce flexion in the knee and rotation in the hip joint so the afflicted person may learn or relearn normal ambulatory movements. This is accomplished by immobilizing the ankle and foot from a point below the knee joint or tibial tubercle to proximate the metatarsal phalengeal joint or metatarsal head while the same are in a neutral position of maximal joint congruency.

The metatarsal heads or joints are accommodated to avoid force applying contact with a supporting sole to thereby obviate muscle spasms. Muscle spasm is further minimized by supporting the toes of the foot in a relaxed muscle position. Normal ambulation is encouraged and is induced by a novel sole that directs the fused foot and leg through desired predetermined ambulating movements.

The above description, as well as further objects, features and advantages of the present invention, will be more fully appreciated by reference to the following detailed description of a presently preferred, but nonetheless illustrative, embodiment in accordance with the present invention when taken in conjunction with the accompanying drawings wherein:

FIG. 1 is a perspective view of an orthotic device according to the present invention;

FIG. 2 is a perspective view of the walking outer sole of the orthosis;

FIG. 3 is a view from a lateral side of the orthotic device;

FIG. 4 is a posterior view; and

Figures 5, 6:
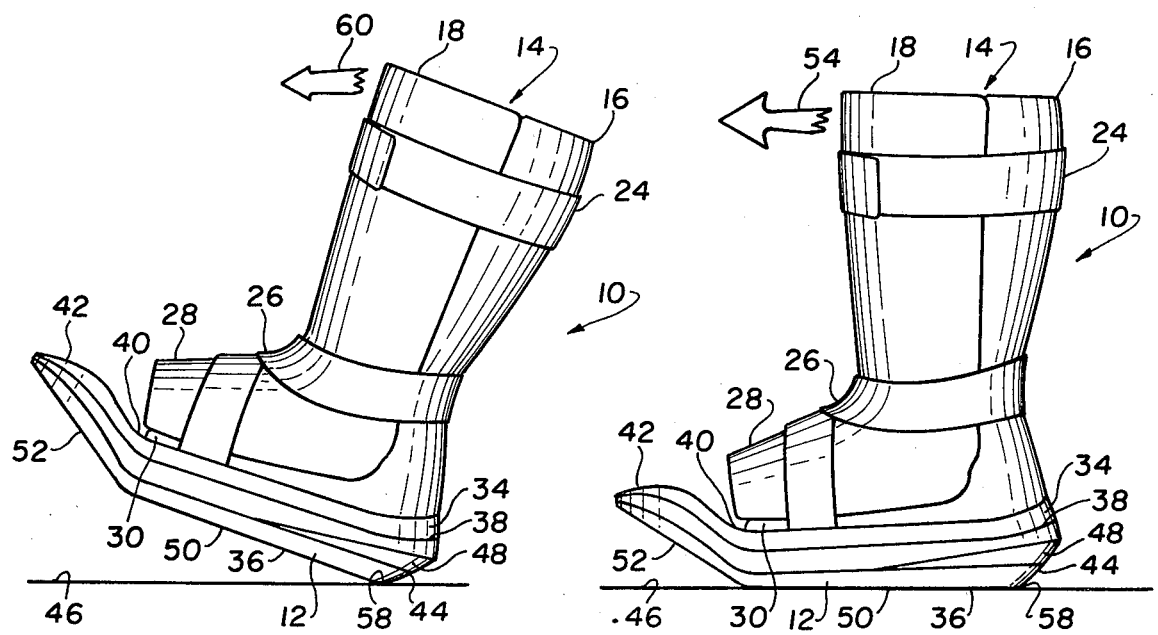
FIGS. 5 to 7 illustrate the heel contact, mid-stance and toe movements of the orthotic device.

Referring now to the drawings, the present orthotic device, more aptly identified as a tone reducing the ankle-foot orthotic device, is generally identified by the numeral 10. The orthotic device 10 comprises a sole generally identified by the numeral 12 and an immobilizing boot generally identified by the numeral 14. The sole structure 12 may be made of any convenient soft or yieldable shock absorbent material as neoprene or the like that is molded to the shape of the sole of the foot of the wearer (not shown).

Integrally connected with the sole structure 12 is the boot structure 14 that is formed in a plurality of shells or parts here shown as a posterior shell 16 and an anterior shell part 18. The two parts of the boot 14 are separable but cooperable with each other in a manner as will be described. However, the posterior shell part 16 is intended to be secured to and to form an integral part of the sole structure 12. In practice, they may actually be molded as a unitary structure.

The boot structure 14 is made to conform exactly to the shape and configuration of the ankle and foot of the leg of the afflicted person by molding or casting the same thereto while the foot and ankle are in their neutral position. The neutral position is here defined as that position in which the muscles of the patient or wearer are most relaxed and the subtalor joints thereof in maximal congruency or joint-to-joint contact. This means, therefore, that the boot structure 14 is intended to enclose and hold the foot, ankle, and the leg above the ankle in the most relaxed position of the patient so as to enable the patient to utilize the present orthotic device 10 while the muscles throughout the leg and foot are fully relaxed.

This is accomplished by first making a mold or cast of the leg from a point below the knee joint or tibial tubercle fully down across and about the ankle and along the foot to the distal aspect 20 of the boot 14 that falls just proximal to the metatarsal phalangeal joint or metatarsal head of the wearer's foot. This means that when the wearer's leg, ankle and foot are enclosed within the boot 14, the metatarsal phalangeal joint of the foot projects anteriorly outward and beyond the distal aspect 20 of the boot so that the metatarsal phalangeal joint or heads are free of touching engagement with the enclosing boot 14.

By forming the boot structure 14 in two parts 16 and 18, access to and from the boot is made easier and less painful to the patient or wearer of the same. Thus, it is possible to remove the anterior shell 18 from the posterior shell 16 to permit the leg, ankle and foot to be inserted thereinto without tensing the muscles of the wearer. After the patient's foot is placed within the boot 14, the anterior shell part 18 may be positioned against the posterior shell 16 in the manner as is illustrated in FIG. 1 to overlap one of the shell parts about the other preferably with the anterior shell part overlying the edges of the posterior shell part so as to pull the posterior part snug into full conforming enclosing engagement and relationship about and in supporting relationship with the leg, ankle and foot of the wearer.

Fusing or immobilizing enclosure of the leg, ankle and foot of the wearer is completed by the application of an upper adjustable strap 24 close to or adjacent the upper end of the boot 14 to retain the same tightly and snugly enclosing about the upper portion of the leg below the tibial tubercle. The strap may be mounted to the part 16 at 22 and may be adjustable by the use of a loop shaped buckle adjustment 25. It may include a Velcro or other similar fastening means on the strap 24 to insure its snug, tight retention and closure about the boot parts 16 and 18 without interference with or hindering the ambulating movements of the wearer.

An additional figure "8" type strap 26 may be affixed in the sole structure 12 to extend up and over the instep portion 28 of the anterior shell part 18 that overlies and partially extends down in partial encompassing relationship with the molded forward projecting portion 30 of the posterior shell part 16. The forward projecting portion 30 of the posterior part 16 provides a seat or rest for the foot of the wearer while the anterior instep covering portion 28 presses the foot downward into intimate full conforming contact with the seating portion 30 of the posterior shell part 16 at a point adjacent to the metatarsal digits of the wearer to hold down the metatarsal head region into its desired conforming relationship with the exposed forward portion of the sole 12 that extends beyond the distal aspect 20 of the boot 14.

The figure "8" strap 26 conveniently retains the instep covering portion 28 down into close contact with the foot while enclosing and pulling in the sides of the posterior portion 30 of the shell 16. The strap 26 also extends about and around the back of the boot 14 and about the sides to retain both the posterior and anterior shells 16 and 18 in their desired snug circumposed enclosure about the leg, ankle and foot of the wearer.

The figure "8" strap 26 may have a loop or adjusting buckle 32 that will permit adjustment of the strap snugly into its desired relationship. The ends of the strap may also have Velcro or other fastening means (not shown) that permit the end of the strap to be engaged with the remainder of the strap to prevent the same from flapping loosely into obstructing movement that might otherwise hinder the ambulating movements of the wearer.

Because it is important that the boot 14 conform closely to the neutral position of the leg, ankle and foot of the wearer, so too the sole structure 12 is molded into conforming relationship with the sole of the wearer's foot. For convenience of manufacture, the sole may be made in one or more parts. The upper or insole part 34 thereof is molded precisely to the shape of the sole of the wearer's foot. The lower outer walking sole 36 thereof is so configured as to induce mobilization and apply certain flexor moments, rotations and propulsions to the foot and leg of the wearer.

Although the sole structure 12 may be formed as a single element having the contoured insole 34 and the walking or outer sole 36 shaped to produce the desired effects, it is foreseeable that manufacture of the same can be enhanced by making the insole 34 and the outer sole 36 as separate elements that are later securely jointed together at 38 so as to form the singular or unitary sole structure 12 as shown in the Figs. of the drawings. The supporting surface of the insole part 34 will conform precisely to the shape and contour of the posterior shell part 16 that is integrally connected therewith.

At a point immediately beyond the distal aspect 20 of the forward projecting portions 28 and 30, the insole 34 is provided with a supporting surface that is defined with a crevice or depression 40 (FIG. 1) that extends laterally and substantially fully across the width of the insole 34. The crevice or depression 40 is formed as a smooth gentle curve in the upper supporting surface of the insole 34. It is of such size, shape and depth as to enable it to receive therein and accommodate fully the metatarsal heads of the digits of the foot so that at all times such metatarsal heads are free of such touching and force applying engagement with the orthotic device 10 as to produce muscle spasms or tone. Hence, when the wearer is at ease or at rest, whether standing or sitting, the metatarsal heads will be out of pressure or muscle spasms producing force applying contact with the supporting surface of the insole 34. During ambulation the gentle, smoothly shaped pocket formed by the crevice 40 will accommodate the metatarsal heads and will avoid the production of the debilitating muscle spasms as were produced in the past when the metatarsal heads of the wearer of an orthotic device came into force applying contact with the insole or with a walking surface.

The front or toe portion of the sole structure 12 is provided with a digital supporting platform 42 that may be molded with and as a unitary continuous extension of the sole structure. The digital support platform 42 is raised or elevated in the form of a smooth curve extending upward and forward from and relative to the metatarsal crevice 40 and above the foot support surface of the insole 34. The appearance and smooth, partial S-shaped rising curvature of the digital platform 42 may be more easily seen from the illustrations in FIGS. 3 to 7 inclusive.

The height and curvature of the platform 42 is predeterminately custom shaped to fit its individual wearer in the same manner as were the composite boot 14 and its insole 34. The digital platform 42 begins at substantially the meeting point of the phalanges or digits with the metatarsals. Its shape and contour is determined by supporting the toes in a raised or elevated position of maximal relaxed muscle or minimum muscle tone. The digital platform height and contour is proper when this relaxed muscle or minimum muscle tone condition is achieved by the digital platform 42.

Although each digital platform 42 will be custom made to fit each wearer's specific problem, different digital platform elements 42 may be preformed or molded for commonly encountered problems. The technician shaping the sole structure 12 for use may then select one of the many preformed different digital platform elements 42 as the one best suited to fit and accommodate the user's problem. The selected digital platform element then may be connected to the forward end of the sole structure 12 at the toe end thereof to form an integral working part of the sole structure. Thus, it is foreseeable that the sole structure may be made in a number of parts, one of which may include a separable digital platform element 42 which may be selectively connected to the forward or toe end of the sole structure 12. In this manner, numerous preformed interchangeable digital platform elements 42 may be inexpensively provided and made in mass production.

The outer or walking sole 36 of the sole structure 12 is preferably provided throughout its length with a non-slip, grid-type surface material that is shaped to provide a rocking platform for the wearer of the device 10. The rocking outer sole platform 36 applies a mobilizing effect to the foot and leg of the wearer in spite of the fact that the foot and ankle are fused and immobilized in the enclosure provided by the boot structure 14.

The heel of the outer sole 36 is contoured to slope or taper downward and forward such as is illustrated at 44 and seen more clearly in FIGS. 3 to 7. The sloped heel 44 initiates and induces the user to lower the heel of the boot 14 into its initial walking contact with a walking surface 46 as is identified in FIGS. 5 to 7. Lateral tilt and rotation may be induced and imparted to the foot by the strategic introduction and interposition of varus posting or wedges 48 in the heel portion of the sole structure 12 as is illustrated in FIGS. 3 and 4. Those skilled in the art will readily recognize that the points at which the varus posting is applied to the support provided by the sole structure 12 to the foot of the wearer may be selectively varied to effect different lateral tilts and rotations to the foot and leg depending upon the results desired.

Merging with the end of the slope 44 of the heel is a mid-stance substantially flat longitudinally extending portion 50 of the outer walking sole 36. The mid-stance portion 50 of the outer sole is substantially flat to provide the wearer with an area of stability upon which the wearer may stand without rocking forward or rearward should he desire to stand in one place. However, the extent of the mid-stance surface portion 50 is such as not to interfere with or stop the induced rocking motion that will be applied to the boot of the wearer during desired and deliberate ambulation.

The substantially flat mid-stance portion 50 merges with a forward rocking portion 52 that is an angularly raised undersurface of the lateral digital platform 42. Although the exposed outer toe or forward rocking portion 52 may be curved substantially conforming to the shape of the curve of the digital supporting platform 42, in practice it has been found that when the surface 52 is made substantially flat rather than upwardly curved to the shape of the digital platform 42, the relatively flat surface 52 provides greater stability to the wearer when the same comes into contact with the walking surface 46 therebeneath. The surface 52 is provided at a predetermined angle to the mid-stance surface portion 50 so as to apply a desired flexion to the leg and knee during the forward propulsion of the foot. The direction of this flexor moment is illustrated in FIG. 6 by the arrow 54.

Figure 7:
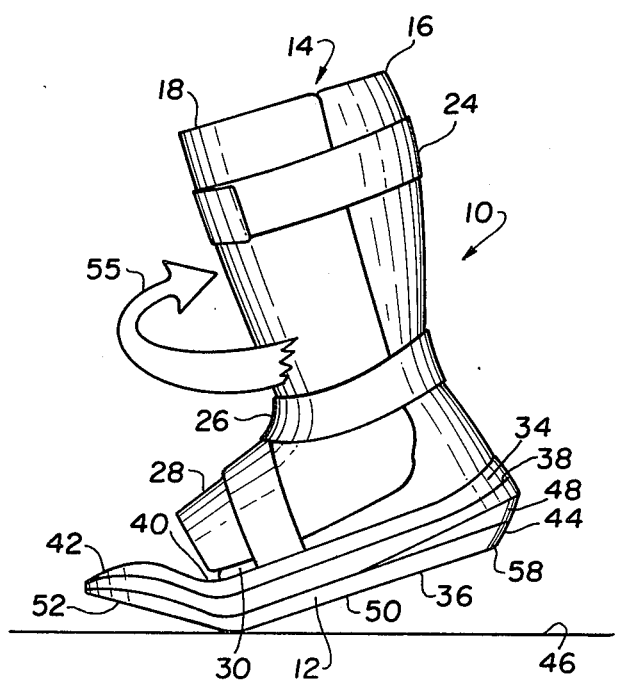

The rocking surface 52 has the ability to induce the foot to move through a lateral rotation as shown at arrow 55 in FIG. 7 to produce rotation of the leg at the hip and hip extension. To accomplish this, the surface 52 may be provided with what is known as a metatarsal break angle more clearly illustrated in FIG. 2 by the numeral 56. The metatarsal break angle 56 may be formed by the application of one or more wedges strategically and predeterminately positioned within the sole structure 12 beneath the digital supporting platform 42 for engagement with the walking surface 46 or in the alternative by the removal of a selected portion of the sole 36. Thus, in FIG. 2 the break angle 56 there shown will induce an out-toe or toe-out movement. By reversing the build up or removal of portions of the sole on the opposite side of the sole, the break angle can be changed to induce an in-toe or toe-in movement. By building up the forward rocking surface 52, it is possible to cause the built up side of the surface 52 to engage with the walking surface 46 first so as to cause the lateral digital platform 42 and the foot mounted thereon to rotate laterally in the direction opposite to and away from the metatarsal break angle. This causes the foot to move to correct either a toe-in or a toe-out condition of the wearer.

For example, if the wearer has an extreme toe-out condition, wedges may be provided on the lateral outer side of the sole structure 12 in the area of the walking sole surface 52 to cause the foot to toe-in. Where the wearer has a toe-in condition that must be corrected, wedges may be applied to the lateral inner side of the surface 52 to cause the foot of the wearer to toe-out when the surface 52 comes into rocking contact with the walking surface 46. Naturally the extent and height of the metatarsal break angle 56 will be custom fit to each wearer. Hence, the extent of the angle may vary from time to time as the toe-in or toe-out condition of the wearer changes.

In practice FIG. 5 illustrates a short portion of the position of initial contact between the sloped heel 44 of the device 10 with the walking surface 46 initiated during ambulation. At such time, by reason of the forward movement of the wearer, the device 10 rocks about the point of heel contact 58 with the walking surface 46. The foot is automatically propelled in a forward direction such as is indicated by the arrow 60.

As the foot and ankle continue in their further progress of propulsion, they pass through the mid-stance position as is illustrated in FIG. 6. Where a (forward) flexor moment 54 is required to be applied to the leg and knee, the outer sole may be thickened or increased in thickness from the mid-stance portion 50 toward the heel 44. The momentum of the forward propulsion and movement then aids the rocking platform 36 to continue in its forward propulsion to and beyond the mid-stance position as indicated in FIG. 6 where the rocking surface 52 of the digital supporting platform 42 moves downward toward and subsequently into engagement with the walking surface 46. As the metatarsal break angle 56 comes into contact with the walking surface 46, depending upon the position and nature of the wedging or removal of sole at the metatarsal break angle, the wearer's foot will be caused to perform a lateral rotation 55 either to correct a toe-in or a toe-out condition.

During these forward propulsion movements afforded by the rocking platform 36, the wearer's knee is taught to bend and flex, and the hip and hip extensions are taught to rotate and pivot in the same manner as do the knees, hips and hip extensions of normal people. This learning process takes but a relatively short period of time even for persons who are afflicted with neurological problems. After a relatively short period of use of the orthotic device 10, the wearer finds himself lowering the arms downward toward the side and extending them in a swinging motion that approximates that of a normal person.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. An ankle-foot orthosis comprising
means immobilizing the ankle and foot against relative movement,
foot support means connected with said immobilizing means,
said immobilizing means and foot support means being formed to the configuration of the neutral position of maximal subtalor joint contact and relaxed muscle of the ankle and foot of the wearer,
and said foot support having means to support the foot with the metatarsal heads thereof normally out of muscle spasm producing contact with said foot support while the toes of the foot are supported in a position of relaxed muscle.

2. An ankle-foot orthosis as in claim 1,
said immobilizing means extending from the tibial tubercle of a wearer to proximate the metatarsal phalangeal joint for fusing together the wearer's ankle and foot therebetween.

3. An ankle-foot orthosis as in claim 2,
said immobilizing means being a boot having a posterior part integral with said foot support and forming a foot supporting part thereof and an openable anterior part for providing access to the interior of said posterior part, for connection with said posterior part for receiving a wearer's ankle and foot therein and for immobilizing the same against relative movement therebetween.

4. An ankle-foot orthosis as in claim 3,
and means cooperating with said boot parts to releasably connect the same together.

5. An ankle-foot orthosis as in claim 1,
said means supporting the wearer's foot on said foot support being a surface having a depression defined therein to receive and support the metatarsal heads of the digits of the foot so that the metatarsal heads are free of muscle spasm producing contact with said foot support surface during ambulation.

6. An ankle-foot orthosis as in claim 5,
said foot support surface having a laterally disposed platform raised from the meeting point of the phalanges with the metatarsals to substantially the ends of the toes of the foot of the wearer to raise the toes to a position wherein the muscles of the toes are relaxed.

7. An ankle-foot orthosis as in claim 1,
said foot support including a platform for supporting the toes raised in a position of relaxed muscle.

8. An ankle-foot orthosis as in claim 1,
said foot support having an outer sole platform extending from the heel of said foot support to approximately the metatarsal phalangeal joint to cause the foot to rock in a forward direction when the heel thereof comes into engagement with a walking surface,
and said outer sole platform having a rock angle raised from the walking surface and with respect to said outer sole platform to cause the toes of the foot to rock forward and downward toward the walking surface to apply a flexor moment to the leg.

9. An ankle-foot orthosis as in claim 8,
and means on said rock angle to engage the walking surface to cause the foot to rotate laterally as said rock angle engages a walking surface.

10. A method of inducing pivotal movements at the knee and lateral rotations at the hip comprising
supporting the foot and ankle of a person against relative movement in a position of subtalor maximal joint contact and relaxed muscle with the metatarsal heads of the digits of the foot free of muscle spasm producing contact with a sole that maintains the toes of the foot in a position of relaxed muscle,
and during ambulation causing the foot to rock forward from the heel thereof upon contact with a walking surface to apply a flexor moment to the leg as the same moves beyond a mid-stance position and continued ambulation causes the toes to propel in a downward direction toward contact with the walking surface.

11. A method as in claim 10,
varying points of support of the foot to induce predetermined amounts of flexion of the knee, hip and extensions thereof during ambulation.

12. A method as in claim 10,
varying the angle at which the toes move toward a walking surface to induce a predetermined lateral rotation of the foot, the knee, the hip and extensions thereof.

13. A method as in claim 10,
immobilizing the foot and ankle against relative movement from the tibial tubercle of the leg to proximate the metatarsal phalangeal joint.

14. A method as in claim 10,
positioning the metatarsal heads of the digits of the foot so the same are within the defines of a depression and out of muscle spasm producing contact with the sole.

15. An orthotic device for teaching normal ambulation to a wearer by supporting the ankle and foot, the combination comprising
a sole for supporting the foot,
a boot comforming to and enclosing the ankle and foot in an immobile relationship in which the same are fused against relative movement by said conforming boot from proximal the metatarsal phalangeal joint of the foot substantially to the tibial tubercle of the leg while the subtalor joints thereof are in a position of maximal contact and produce relaxed muscle, and means cooperating with said boot to retain the same releasably and conformingly enclosed about the ankle and foot during ambulation.

16. An orthotic device as in claim 15, said boot having a plurality of parts including a posterior shell integral with said sole and an anterior shell movable into and out of conforming relationship with the posterior shell to releasably enclose the ankle and foot therein, and said retaining means releasably retaining said shells in their enclosing relationship.

17. An orthotic device for teaching normal ambulation to a wearer by supporting the ankle and foot, the combination comprising a sole for supporting the foot, said sole including means to support the foot with the metatarsal digits thereof out of muscle spasm producing contact during ambulation, a boot conforming to and enclosing the ankle and foot in an immobile relationship in which the same are fused against relative movement by said conforming boot from proximal the metatarsal phalangeal joint of the foot substantially to the tibial tubercle of the leg while the subtalor joints thereof are in a position of maximal contact and produce relaxed muscle, and means cooperating with said boot to retain the same releasably and conformingly enclosed about the ankle and foot during ambulation.

18. An orthotic device as in claim 17, said included means of said sole being a depression defined in said sole to receive the metatarsal digits therein free of force applying contact with said sole.

19. An orthotic device for teaching normal ambulation to a wearer by supporting the ankle and foot, the combination comprising a sole for supporting the foot, means on said sole supporting the toes of the foot in a position of relaxed muscle, a boot conforming to and enclosing the ankle and foot in an immobile relationship in which the same are fused against relative movement by said conforming boot from proximal the metatarsal phalangeal joint of the foot substantially to the tibial tubercle of the leg while the subtalor joints thereof are in a position of maximal contact and produce relaxed muscle, and means cooperating with said boot to retain the same releasably and conformingly enclosed about the ankle and foot during ambulation.

20. An orthotic device as in claim 18, said toes supporting means being a platform raised above the metatarsal digits of the foot supported on said sole.

21. An orthotic device as in claim 15, said sole having an outer walking sole with a flat portion along the mid-length thereof extending from the heel and having a merging rocking platform beneath the toes of the foot raised from said walking sole so that during ambulation the foot thereon is caused to rock from the heel toward the toes to pass through a mid-stance position to propel the foot forward so that said rocking platform is caused to move downward toward a walking surface to cause the knee to experience flexor moments.

22. An orthotic device comprising the combination of a sole having a foot supporting insole and immobilizing means connected with said sole to retain a foot supported on said sole and its related ankle against relative movements in a position of maximal subtalor joint contact and relaxed muscle, said insole having means to support a foot thereon with the metatarsal digits thereof free of muscle spasm producing contact therewith when the foot and ankle are supported in their position of maximal subtalor joint contact and relaxed muscle, and toe supporting means on said insole for supporting the toes of the foot in a position of relaxed muscle.

23. An orthotic device as in claim 22, said insole foot support means being a depression disposed laterally across said insole and being of a length and width to receive the foot metatarsal digits therein such that the digits are out of force applying engagement with the insole during ambulation.

24. An orthotic device as in claim 23, said toe supporting means being a platform for supporting the toes in the position raised above the metatarsal digits.

25. An orthotic device as in claim 24, said immobilizing means including a plurality of separable parts one of which is connected with said sole and the other of which is separable from said one part to enable the application of the first part and said sole to a wearer's foot and ankle and for immobilized enclosure of the same by the return of said other part to said first part, and means cooperating with said parts to retain the same together to enclose the foot and ankle immobilized therein.

26. An orthotic device as in claim 23, said sole having a walking outer sole with means at the heel thereof to induce the foot to rock forward to a mid-stance position, a substantially flat surface on said sole between the heel and toe thereof, and a platform raised above said substantially flat surface and beneath said toe supporting means to induce the foot to rock forward at the toes.

27. An orthotic device as in claim 26, and means on said walking platform engageable with a walking surface during ambulation to cause the foot to move through a lateral rotation.

28. An orthotic device as in claim 21, said rocking platform being configured and dimensioned so that during ambulation it causes the foot to rotate laterally as said rocking platform engages a walking surface.

* * * * *